United States Patent [19]

Shibata et al.

[11] Patent Number: 5,789,428
[45] Date of Patent: Aug. 4, 1998

[54] AMINO-ACID AMIDE DERIVATIVES, PROCESSES FOR PREPARING THE SAME, AGRICULTURAL OR HORTICULTURAL FUNGICIDES, AND METHOD FOR KILLING FUNGI

[75] Inventors: Masaru Shibata; Kazuhiko Sugiyama; Norihisa Yonekura, all of Iwata-gun; Junetsu Sakai, Ogasa-gun; Yoshiyuki Kojima, Kakegawa; Shigeru Hayashi, Ogasa-gun, all of Japan

[73] Assignees: Kumiai Chemical Industry Co. Ltd.; Ihara Chemical Industry Co., Ltd., both of Tokyo, Japan

[21] Appl. No.: 776,387

[22] PCT Filed: May 23, 1995

[86] PCT No.: PCT/JP95/00981

§ 371 Date: Feb. 3, 1997

§ 102(e) Date: Feb. 3, 1997

[87] PCT Pub. No.: WO96/04252

PCT Pub. Date: Feb. 15, 1996

[30] Foreign Application Priority Data

Aug. 3, 1994 [JP] Japan .................. 6-202762
Oct. 25, 1994 [JP] Japan .................. 6-283961

[51] Int. Cl.$^6$ .................. A01N 43/52; A01N 43/76; A01N 43/78; C07D 235/16; C07D 263/56
[52] U.S. Cl. .................. 514/367; 514/375; 514/394; 548/178; 548/180; 548/217; 548/309.7
[58] Field of Search .................. 548/178, 180, 548/217, 309.7; 514/375, 367, 394

[56] References Cited

U.S. PATENT DOCUMENTS

| | | | |
|---|---|---|---|
| 5,158,962 | 10/1992 | Seitz et al. | 514/335 |
| 5,395,824 | 3/1995 | Higuchi et al. | 514/19 |
| 5,428,167 | 6/1995 | Wissner et al. | 546/146 |
| 5,430,150 | 7/1995 | Trova et al. | 546/139 |

FOREIGN PATENT DOCUMENTS

| | | |
|---|---|---|
| 337714 | 10/1989 | European Pat. Off. |
| 4321897 | 1/1995 | Germany |
| 5-140063 | 6/1993 | Japan |

OTHER PUBLICATIONS

Maekawa et al., Agric. Biol. Chem., 41 (5), 811–818, 1977.
Maekawa et al., Chemical Abstracts, 87:202070, 1977.
Vermehren et al., Chemical Abstracts, 122:133844, 1995.

Primary Examiner—Fiona T. Powers
Attorney, Agent, or Firm—Oblon, Spivak, McClelland, Maier & Neustadt, P.C.

[57] ABSTRACT

The present invention provides an amino-acid amide derivative represented by the formula:

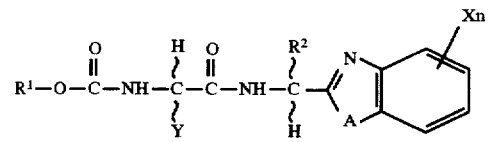

(wherein $R^1$ represents a C1–C6 alkyl group, a C3–C8 cycloalkyl group, or a phenyl group, $R^2$ represents a hydrogen atom or a methyl group, X represents a halogen atom, a methyl group, a methoxy group, Y represents a C1–C6 alkyl group, A represents an oxygen atom, or a sulfur atom, and n represents 0 or an integer from 1 to 3), an agricultural or horticultural fungicide including an effective amount of the same, and a method for killing agriculturally or horticulturally harmful fungi which comprises a step of using a fungicidally effective amount of the amino-acid amide derivative. The present invention provides the amino-acid amide derivatives, which exhibit superior control of plant diseases such as late blight and downy mildew, and which are not harmful chemicals.

7 Claims, No Drawings

5,789,428

AMINO-ACID AMIDE DERIVATIVES, PROCESSES FOR PREPARING THE SAME, AGRICULTURAL OR HORTICULTURAL FUNGICIDES, AND METHOD FOR KILLING FUNGI

FIELD OF THE INVENTION

The present invention relates to novel amino-acid amide derivatives and to processes for their preparation. The present invention also relates to agricultural or horticultural fungicides containing the same as active ingredients and to a method for killing fungi.

BACKGROUND ART

Heretofore, it is known that amino-acid amide derivatives, such as, for example, $N^1$-[1-(2-furanyl)ethyl]-$N^2$-phenoxycarbonyl-L-valinamide are useful as biocides (Japanese Patent Application, First Publication, No. Hei 3-153657). In addition, it is also known that amino-acid amide derivatives, such as, for example, $N^1$-[1-(2-benzo[b]thienyl)ethyl]-$N^2$-benzyloxycarbonyl-L-valinamide, $N^2$-tert-butoxycarbonyl-$N^1$-[1-(3-chloro-2-benzofuranyl)ethyl]-L-valinamide are useful for fungicides (European Patent No. 587110).

However, the fungicidal activities of fungicides may decrease because of the emergence of resistant fungi after repeated use of the fungicides. For this reason, as well as because of environmental problems, it is desired to provide novel fungicides which can efficiently control harmful fungi even at low concentrations.

DISCLOSURE OF THE INVENTION

In order to develop fungicides possessing fungicidal activities superior to those of known fungicides, the present inventors have synthesized various amino-acid amide derivatives and have carried out extensive research in connection with their effects on the physiological activities of fungi. As a result, we have found that the compounds according to the present invention, possessing a benzothiazole ring, a benzoxazole ring, or a benzimidazole ring bonded to an amine moiety, exhibit a broad spectrum of anti-fungal activity at low dose especially against tomato late blight, potato late blight, grape downy mildew, and cucumber downy mildew, while at the same time do not hinder desirable plant growth.

According to aspects of the present invention, there are provided (1) an amino-acid amide derivative represented by the formula:

[I]

wherein $R^1$ represents a C1–C6 alkyl group, a C3–C8 cycloalkyl group, a phenyl group (optionally having at least one same or different halogen atom substituent), or a benzyl group, $R^2$ represents a hydrogen atom or a methyl group, X represents a halogen atom, a methyl group, a methoxy group, a methylthio group, a cyano group, or a trifluoromethyl group, Y represents a C1–C6 alkyl group, A represents an oxygen atom, a sulfur atom, or a group of the formula:

$$-\underset{|}{N}R^3$$

(wherein $R^3$ represents a hydrogen atom, a C1–C6 alkyl group, a C1–C6 alkoxymethyl group, or an acyl group), and n represents 0 or an integer from 1 to 3.

(2) a process for preparing an amino-acid amide derivative represented by the formula:

[I]

(wherein $R^1$, $R^2$, X, Y, A, and n have the same meanings as defined in (1)), comprising a step of reacting an amino-acid amide derivative represented by the formula:

[II]

(wherein $R^1$ and Y have the same meanings as defined above), or the amino-acid amide derivative possessing an activated carboxyl group, with an amine represented by the formula:

[III]

(wherein $R^2$, X, A, and n have the same meanings as defined above), in the presence of catalysts and/or bases if necessary.

(3) a process for preparing an amino-acid amide derivative represented by the formula:

[I]

(wherein $R^1$, $R^2$, X, Y, A, and n have the same meanings as defined above), comprising a step of reacting a compound represented by the formula:

$$R^1-O-\underset{\|}{\overset{O}{C}}-Z$$  [IV]

(wherein Z represents a halogen atom or a group of the formula: $R^1OC(O)O-$, $R^1$ has the same meaning as defined above), with an amine represented by a formula:

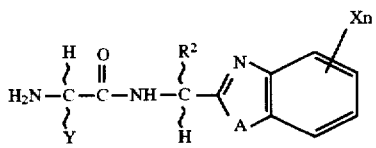

(wherein $R^2$, X, Y, A, and n have the same meanings as defined above),
or an inorganic acid salt thereof including a hydrochloride or an organic acid salt thereof including a tosylate in the presence of a base if necessary, (4) an agricultural or horticultural fungicide including the amino-acid amide derivative as defined above as an active ingredient, and (5) a method for killing agriculturally or horticulturally harmful fungi which comprises a step of using a fungicidally effective amount of an amino-acid amide derivative as defined above.

The terms employed in this specification of the present invention are defined as follows.

The term "alkyl group" is used herein to mean a straight or branched alkyl group possessing 1 to 6 carbon atoms including, but not limited to, a methyl group, ethyl group, propyl group, isopropyl group, butyl group, isobutyl group, sec-butyl group, tert-butyl group, pentyl group, 1-methylbutyl group, 2-methylbutyl group, 3-methylbutyl group, 2,2-dimethylpropyl group, 1,1-dimethylpropyl group, 1-ethylpropyl group, hexyl group, isohexyl group, or the like.

The term "halogen atom" is used herein to mean a fluorine atom, chlorine atom, bromine atom, iodine atom, or the like.

The term "cycloalkyl group" is used herein to mean a cycloalkyl group possessing 3 to 8 carbon atoms and including, but not limited to, a cyclopropyl group, cyclobutyl group, cyclopentyl group, cycloheptyl group, cyclooctyl group, or the like.

The term "alkoxymethyl group" is used herein to mean a straight or branched alkoxymethyl group possessing 1 to 6 carbon atoms and including, for example, a methoxymethyl group, ethoxymethyl group, propoxymethyl group, isopropoxymethyl group, butoxymethyl group, isobutoxymethyl group, sec-butoxymethyl group, or the like.

The term "acyl group" is used herein to mean an acetyl group, benzoyl group, or the like.

The compounds represented by Formula [I] according to the present invention can exist as stereoisomers by virtue of the presence of one or two asymmetric carbon atoms, which can be separated by appropriate methods. The present invention includes all such stereoisomers, including diastereomers, enantiomers, and mixtures thereof.

As the preferred compounds represented by Formula [I], $R^1$ represents a straight or branched alkyl group possessing 2 to 6 carbon atoms or a phenyl group; $R^2$ represents a hydrogen atom or a methyl group; X represents a halogen atom; Y represents an isopropyl group; A represents a sulfur atom; n represents an integer of 0 or 1; and the amino acid is an L-isomer. The particularly preferred compound is $N^1$-[(R)-1-(6-fluoro-2-benzothiazolyl)ethyl]-$N^2$-isopropoxycarbonyl-L-valinamide.

Next, representative examples of the compounds represented by Formula [I] according to the present invention are listed in Table 1. However, it should be understood that the invention is not limited to these compounds. The compound Numbers given in Table I will be referred to in the subsequent description.

TABLE 1

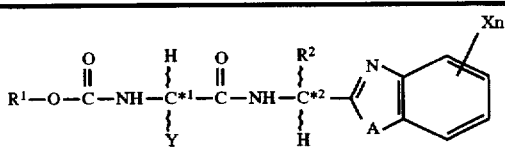

| Compound No. | $R^1$ | $R^2$ | Y | A | Xn | Physical Constants Melting Point (°C.) |
|---|---|---|---|---|---|---|
| 1 | $C_3H_7$-i | H | $C_3H_7$-i | S | H | 190–191 |
| 2 | $C_3H_7$-i | H | $C_3H_7$-i | S | 6-F | |
| 3 | $C_3H_7$-i | $CH_3$ | $C_3H_7$-i | S | 4-F | 186–189 |
| 4 | $C_3H_7$-i | $CH_3$ | $C_3H_7$-i | S | 6-F | 167–168 |
| 5 | $C_3H_7$-i | $CH_3$ | $C_3H_7$-i | S | 7-F | |
| 6 | $C_3H_7$-i | $CH_3$ | $C_3H_7$-i | S | 6-Cl | 194–195 |
| 7 | $C_3H_7$-i | $CH_3$ | $C_3H_7$-i | S | 4-Cl | 188–190 |
| 8 | $C_3H_7$-i | $CH_3$ | $C_3H_7$-i | S | 7-Cl | |
| 9 | $C_3H_7$-i | $CH_3$ | $C_3H_7$-i | S | 6-$CH_3$ | 190–192 |
| 10 | $C_3H_7$-i | $CH_3$ | $C_3H_7$-i | S | 6-$OCH_3$ | 205–207 |
| 11 | $C_3H_7$-i | $CH_3$ | $C_3H_7$-i | S | 5, 6-$(CH_3)_2$ | |
| 12 | $C_3H_7$-i | $CH_3$ | $C_3H_7$-i | O | 5-$CH_3$ | |
| 13 | $C_3H_7$-i | $CH_3$ | $C_3H_7$-i | NH | 5-F | 105–108 |
| 14 | $C_3H_7$-i | $CH_3$ | $C_3H_7$-i | NH | 5-$CH_3$ | 110–112 |
| 15 | $C_4H_9$-t | H | $C_3H_7$-i | S | H | 133–134 |
| 16 | $C_4H_9$-t | H | $C_3H_7$-i | S | 6-F | |
| 17 | $C_4H_9$-t | $CH_3$ | $C_3H_7$-i | S | 6-F | 128–129 |
| 18 | $C_4H_9$-t | $CH_3$ | $C_3H_7$-i | S | 6-$CH_3$ | 122–124 |
| 19 | $C_4H_9$-t | $CH_3$ | $C_3H_7$-i | S | 6-$OCH_3$ | 145–147 |
| 20 | $C_4H_9$-t | $CH_3$ | $C_3H_7$-i | S | 5, 6-$(CH_3)_2$ | |
| 21 | $C_4H_9$-t | $CH_3$ | $C_3H_7$-i | S | 6-Cl | 133–134 |
| 22 | $C_4H_9$-t | $CH_3$ | $C_3H_7$-i | S | 4-Cl | 110–112 |
| 23 | $C_4H_9$-t | $CH_3$ | $C_3H_7$-i | O | 5-$CH_3$ | |

TABLE 1-continued $$R^1-O-\overset{O}{\underset{}{C}}-NH-\overset{H}{\underset{Y}{C^{*1}}}-\overset{O}{\underset{}{C}}-NH-\overset{R^2}{\underset{H}{C^{*2}}}-\underset{A}{\overset{N}{\diagdown}}\!\!\!\diagup\!\!\!\!-X_n$$

| Compound No. | $R^1$ | $R^2$ | Y | A | Xn | Physical Constants Melting Point (°C.) |
|---|---|---|---|---|---|---|
| 24 | $C_4H_9$-t | $CH_3$ | $C_3H_7$-i | NH | 5-F | 207–208 |
| 25 | $C_4H_9$-t | $CH_3$ | $C_3H_7$-i | NH | 5-$CH_3$ | 114–116 |
| 26 | $C_4H_9$-t | $CH_3$ | $C_3H_7$-i | NC(O)$CH_3$ | H | 140–142 |
| 27 | $C_4H_9$-t | $CH_3$ | $C_3H_7$-i | NC(O)—C$_6$H$_5$ | H | 58–60 |
| 28 | $CH_3$ | $CH_3$ | $C_3H_7$-i | S | H | |
| 29 | $C_2H_5$ | $CH_3$ | $C_3H_7$-i | S | H | |
| 30 | $C_3H_7$-n | $CH_3$ | $C_3H_7$-i | O | H | |
| 31 | $C_3H_7$-i | $CH_3$ | $C_3H_7$-i | S | H | 187–189 |
| 32 | $C_3H_7$-i | $CH_3$ | $C_3H_7$-i | S | H | 180–184 |
| 33 | $C_4H_9$-n | H | $C_3H_7$-i | S | H | |
| 34 | $C_4H_9$-t | $CH_3$ | $C_3H_7$-i | S | H | 66–67 |
| 35 | $C_4H_9$-t | $CH_3$ | $C_3H_7$-i | S | H | |
| 36 | $C_5H_{11}$-n | $CH_3$ | $C_3H_7$-i | S | H | |
| 37 | $C_6H_{13}$-n | $CH_3$ | $C_3H_7$-i | S | 4-$SCH_3$ | |
| 38 | $C_6H_{13}$-i | $CH_3$ | $C_3H_7$-i | S | H | |
| 39 | cyclopropyl | $CH_3$ | $C_3H_7$-i | S | H | |
| 40 | cyclopentyl | $CH_3$ | $C_3H_7$-i | O | H | |
| 41 | cyclohexyl | $CH_3$ | $C_3H_7$-i | S | 4-Cl | |
| 42 | cyclooctyl | H | $C_3H_7$-i | S | H | |
| 43 | phenyl | $CH_3$ | $C_3H_7$-i | S | H | |
| 44 | 4-Cl-phenyl | $CH_3$ | $C_3H_7$-i | S | H | |
| 45 | 4-F-phenyl | $CH_3$ | $C_4H_9$-s | S | H | |
| 46 | 2,4-diCl-phenyl | $CH_3$ | $C_3H_7$-i | S | H | |

TABLE 1-continued

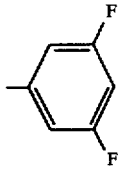

| Compound No. | R¹ | R² | Y | A | Xn | Physical Constants Melting Point (°C.) |
|---|---|---|---|---|---|---|
| 47 | 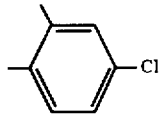 3,5-difluorophenyl | $CH_3$ | $C_3H_7$-i | S | H | |
| 48 | 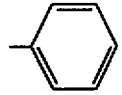 4-chloro-2-fluorophenyl | $CH_3$ | $C_3H_7$-i | S | 5-$CH_3$ | |
| 49 | $C_4H_9$-t | H | $C_3H_7$-i | O | 5-$SCH_3$ | |
| 50 | 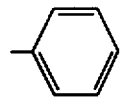 phenyl | H | $C_3H_7$-i | S | 6-$OCH_3$ | |
| 51 | $C_3H_7$-i | $CH_3$ | $C_2H_5$ | O | H | |
| 52 | $C_4H_9$-t | $CH_3$ | $C_2H_5$ | S | H | |
| 53 |  phenyl | $CH_3$ | $C_2H_5$ | S | H | |
| 54 | $C_3H_7$-i | $CH_3$ | $C_4H_9$-s | S | H | |
| 55 | $C_4H_9$-t | $CH_3$ | $C_4H_9$-s | S | H | |
| 56 | 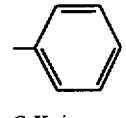 cyclopentyl | $CH_3$ | $C_4H_9$-s | S | H | |
| 57 | $C_3H_7$-i | $CH_3$ | $C_3H_7$-i | O | H | 177–179 |
| 58 | $C_4H_9$-t | $CH_3$ | $C_3H_7$-i | O | H | |
| 59 | 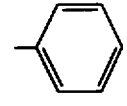 phenyl | $CH_3$ | $C_3H_7$-i | O | H | |
| 60 | $C_3H_7$-i | $CH_3$ | $C_3H_7$-i | NH | 4-$OCH_3$ | |
| 61 | $C_3H_7$-i | $CH_3$ | $C_3H_7$-i | NH | H | 212–214 |
| 62 | $C_4H_9$-t | $CH_3$ | $C_3H_7$-i | NH | H | 217–219 |
| 63 | 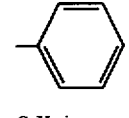 phenyl | $CH_3$ | $C_4H_9$-s | NH | H | |
| 64 | $C_3H_7$-i | $CH_3$ | $C_3H_7$-i | N—$CH_3$ | H | 214–215 |
| 65 | $C_4H_9$-t | $CH_3$ | $C_3H_7$-i | N—$CH_3$ | H | 142–144 |
| 66 | phenyl | $CH_3$ | $C_3H_7$-i | N—$CH_3$ | H | |
| 67 | $C_3H_7$-i | $CH_3$ | $C_3H_7$-i | N—$C_2H_5$ | H | |

TABLE 1-continued

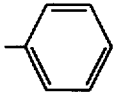

| Compound No. | R¹ | R² | Y | A | Xn | Physical Constants Melting Point (°C.) |
|---|---|---|---|---|---|---|
| 68 | $C_4H_9$-t | H | $C_4H_9$-s | $N-C_2H_5$ | H | |
| 69 | 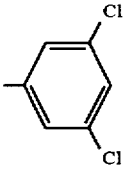 | $CH_3$ | $C_3H_7$-i | $N-C_2H_5$ | 4-$SCH_3$ | |
| 70 | $C_3H_7$-i | H | $C_3H_7$-i | $N-C_3H_7$-n | H | |
| 71 | $C_4H_9$-t | $CH_3$ | $C_3H_7$-i | $N-C_3H_7$-n | H | 162-165 |
| 72 | 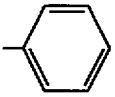 | $CH_3$ | $C_3H_7$-i | $N-C_3H_7$-n | H | |
| 73 | $C_3H_7$-i | $CH_3$ | $C_3H_7$-i | $N-C_3H_7$-i | H | |
| 74 | $C_4H_9$-t | H | $C_3H_7$-i | $N-C_3H_7$-i | 5-F | |
| 75 | 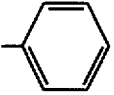 | $CH_3$ | $C_3H_7$-i | $N-C_3H_7$-i | H | |
| 76 | $C_3H_7$-i | $CH_3$ | $C_3H_7$-i | $N-CH_2OCH_3$ | 6-Cl | |
| 77 | $C_4H_9$-t | $CH_3$ | $C_3H_7$-i | $N-CH_2OCH_3$ | H | 152-154 |
| 78 | 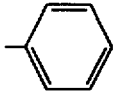 | H | $C_4H_9$-s | $N-CH_2OCH_3$ | H | |
| 79 | $C_3H_7$-i | $CH_3$ | $C_3H_7$-i | $N-CH_2OC_2H_5$ | H | |
| 80 | $C_4H_9$-t | $CH_3$ | $C_3H_7$-i | $N-CH_2OC_2H_5$ | 6-$CH_3$ | |
| 81 | 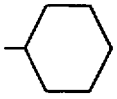 | $CH_3$ | $C_3H_7$-i | $N-CH_2OC_2H_5$ | H | |
| 82 | 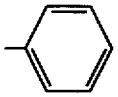 | H | $C_3H_7$-i | $N-COCH_3$ | H | |
| 83 | 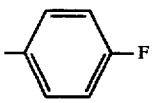 | $CH_3$ | $C_3H_7$-i | $N-COCH_3$ | 4-$OCH_3$ | |
| 84 | $C_4H_9$-t | $CH_3$ | $C_3H_7$-i | S | 4-F | |
| 85 |  | $CH_3$ | $C_4H_9$-s | O | 4-F | |
| 86 | $C_3H_7$-i | $CH_3$ | $C_3H_7$-i | S | 5-F | |
| 87 | $C_4H_9$-t | $CH_3$ | $C_3H_7$-i | O | 5-F | |

TABLE 1-continued

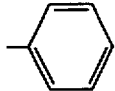

| Compound No. | R¹ | R² | Y | A | Xn | Physical Constants Melting Point (°C.) |
|---|---|---|---|---|---|---|
| 88 | phenyl | $CH_3$ | $C_3H_7$-i | S | 6-F | |
| 89 | $C_3H_7$-i | $CH_3$ | $C_3H_7$-i | S | 5-Cl | 181–183 |
| 90 | $C_4H_9$-t | $CH_3$ | $C_3H_7$-i | S | 5-Cl | 111–112 |
| 91 | phenyl | $CH_3$ | $C_3H_7$-i | S | 5-Cl | 178–180 |
| 92 | $C_3H_7$-i | $CH_3$ | $C_3H_7$-i | O | 5-Cl | |
| 93 | $C_4H_9$-t | $CH_3$ | $C_3H_7$-i | O | 5-Cl | |
| 94 | phenyl | $CH_3$ | $C_3H_7$-i | O | 5-Cl | |
| 95 | $C_3H_7$-i | H | $C_4H_9$-s | S | 6-Br | |
| 96 | $C_4H_9$-t | $CH_3$ | $C_3H_7$-i | S | 6-Br | |
| 97 | $C_3H_7$-i | $CH_3$ | $C_3H_7$-i | S | 5-CN | |
| 98 | $C_3H_7$-i | $CH_3$ | $C_3H_7$-i | S | 6-CN | |
| 99 | 4-Cl-phenyl | H | $C_3H_7$-i | O | 6-Br | |
| 100 | $C_3H_7$-i | $CH_3$ | $C_3H_7$-i | S | 4-$CH_3$ | |
| 101 | cyclohexyl | $CH_3$ | $C_3H_7$-i | O | 4-$CH_3$ | |
| 102 | phenyl | $CH_3$ | $C_3H_7$-i | S | 6-$CH_3$ | |
| 103 | $C_3H_7$-i | $CH_3$ | $C_3H_7$-i | O | 5-$OCH_3$ | |
| 104 | $C_4H_9$-t | H | $C_3H_7$-i | S | 5-$OCH_3$ | |
| 105 | phenyl | $CH_3$ | $C_3H_7$-i | S | 5-$OCH_3$ | |
| 106 | $C_3H_7$-i | $CH_3$ | $C_4H_9$-s | S | 6-$SCH_3$ | |
| 107 | $C_4H_9$-t | $CH_3$ | $C_3H_7$-i | S | 6-$SCH_3$ | |
| 108 | phenyl | H | $C_3H_7$-i | O | 6-$SCH_3$ | |
| 109 | $C_4H_9$-t | $CH_3$ | $C_3H_7$-i | S | 5-$CF_3$ | 115–120 |

TABLE 1-continued $$R^1-O-\overset{O}{\underset{\|}{C}}-NH-\underset{\underset{Y}{|}}{\overset{}{C^{*1}}}-\overset{O}{\underset{\|}{C}}-NH-\underset{\underset{H}{|}}{\overset{R^2}{C^{*2}}}-\underset{A}{\overset{N}{\diagdown}}\!\!\diagup\!\!\!\diagdown\!\!\!\!-X_n$$

| Compound No. | R¹ | R² | Y | A | Xn | Physical Constants Melting Point (°C.) |
|---|---|---|---|---|---|---|
| 110 | —CH₂—⟨phenyl⟩ | CH₃ | C₃H₇-i | S | H | 169–174 |
| 111 | —CH₂—⟨phenyl⟩ | CH₃ | C₃H₇-i | S | H | 160–165 |
| 112 | C₃H₇-i | CH₃ | C₃H₇-i | S | 6-Cl | 198–200 |
| 113 | C₄H₉-t | CH₃ | C₃H₇-i | S | 6-Cl | 128–131 |
| 114 | C₃H₇-i | CH₃ | C₃H₇-i | NH | 5-Cl | 112–115 |
| 115 | C₄H₉-t | CH₃ | C₃H₇-i | NH | 5-Cl | 206–209 |
| 116 | C₃H₇-i | CH₃ | C₃H₇-i | NC₃H₇-n | H | 207–209 |
| 117 | C₃H₇-i | CH₃ | C₃H₇-i | NCH₂OCH₃ | H | 182–184 |

In Table 1, only Compound No. 35 possesses D,L-configurational amino-acid moiety (*¹) and the compounds other than Compound No. 35 possess L-configurational amino-acid moieties. With regard to stereochemical configuration of another asymmetric carbon atom (*²), Compound Nos. 3–4, 6–12, 17–21, 23, 32, and 111 possess R configuration. Compound Nos. 5, 13–14, 22, 24–31, 34–41, 43–48, 51–67, 69, 71–73, 75–77, 79–81, 83–94, 96–98, 100–103, 105–107, 109–110, and 112–117 possess RS configuration.

Next, the preparation processes of the compounds represented by Formula [I] according to the present invention will be explained.

Preparation Process A

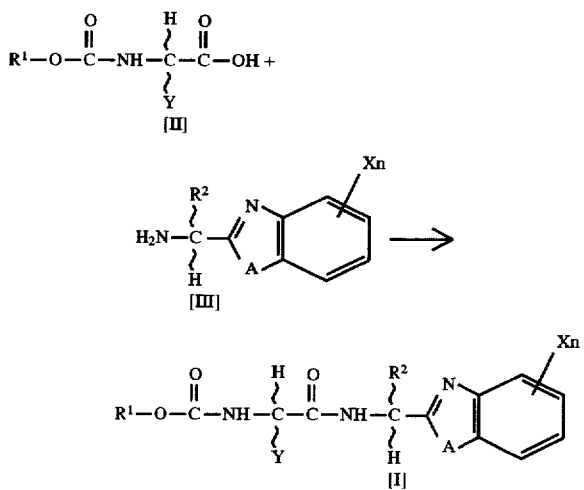

wherein R¹, R², X, Y, A, and n have the same meanings as defined above.

The compounds represented by Formula [I] according to the present invention can be prepared by the reaction of amino acid derivatives represented by Formula [II] or the amino acid derivatives wherein the carboxyl groups are activated, with amines represented by Formula [III] in the presence of catalysts and/or bases, if necessary.

In the present reaction, as the amino acid derivatives represented by Formula [II] with activated carboxyl groups, there can be mentioned, for example, an acid halide such as an acid chloride, an acid anhydride derived by dehydration-condensation of the two molecules of the amino acid derivatives represented by Formula [II], a mixed acid anhydride derived from the amino acid derivative represented by Formula [II] and another acid or an O-alkyl carbonic acid, and an activated ester such as p-nitrophenyl ester, 2-tetrahydropyranyl ester, and 2-pyridyl ester and the like.

In addition, it is also possible to perform the present reaction using a condensing agent such as N,N'-dicyclohexylcarbodiimide, N,N'-carbonyldiimidazole, 2-chloro-1,3-dimethylimidazolium chloride, or the like.

The present reaction can be performed in a conventional solvent. This solvent can be any solvent that does not hinder the reaction, for example, hydrocarbons such as pentane, hexane, heptane, cyclohexane, petroleum ether, ligroin, benzene, toluene, xylene and the like, halogenated hydrocarbons such as methylene chloride, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, acetates such as methyl acetate, ethyl acetate and the like, nitriles such as acetonitrile, propionitrile, benzonitrile and the like, aprotic polar solvents such as dimethylsulfoxide, N,N-dimethylformamide, sulfolane and the like, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, organic bases such as triethylamine, trimethylamine, N,N-dimethylaniline, pyridine, N-methylpiperidine, 1,5-diazabicyclo [4.3.0] non-5-ene (DBN), 1,8-diazabicyclo[5.4.0] undec-7-ene (DBU), and the like, and preferably tertiary amines such as triethylamine, N-methylpiperidine, pyridine, N-methylpiperidine or the like.

As the catalyst, there can be mentioned, for example, 4-dimethylaminopyridine, 1-hydroxybenzotriazole, N,N-dimethylformamide and the like.

The present reaction is carried out at a temperature range of from −75° C. to 100° C., and preferably from −60° C. to 40° C. The reaction time is preferably 1 to 20 hours.

Next, the preparation processes for the starting materials employed in the present invention will be explained in the following.

The compounds represented by Formula [II] can be prepared, for example, by means of the reaction of L-valine with di(tert-butyl) dicarbonate in the presence of sodium bicarbonate, affording N-tert-butoxycarbonyl-L-valine, or by means of the reaction of DL-valine and carbobenzoxy chloride in the presence of sodium bicarbonate, affording N-benzyloxycarbonyl-DL-valine. These methods have been known [for example, see *Methoden der Organischen Chemie*, Vol. 15, No. 2, page 2; Georg Thieme Verlag Stuttgart: 1974; *Chemistry of the Amino Acids*, vol. 2, page 891; John Wiley & Sons, N.Y (1964); and *Journal of the American Chemical Society*, Vol. 79, page 4686 (1957)].

In addition, among the compounds as starting materials wherein the carboxyl groups of the amino acid derivatives are activated, for example, a mixed acid anhydride can be prepared by the reaction of the amino acid derivatives represented by Formula [II] and pivaloyl chloride in the presence of an organic base. p-Nitrophenyl esters can be prepared by the reaction of the amino acid derivatives represented by Formula [II] and p-nitrophenol in the presence of condensing agents.

These methods have been known [for example, see *Methoden der Organischen Chemie*, Vol. 15, No. 2, page 2; Georg Thieme Verlag Stuttgart: 1974; *Chemische Berichte*, Vol. 38, page 605 (1905); *Journal of the American Chemical Society*, Vol. 74, page 676 (1952); and *Journal of the American Chemical Society*, Vol. 86, page 1839 (1964)].

Condensed hetero-cycle derivatives represented by Formula [III] can be manufactured, for example, by the following reaction scheme:

Preparation Process A for Starting Material

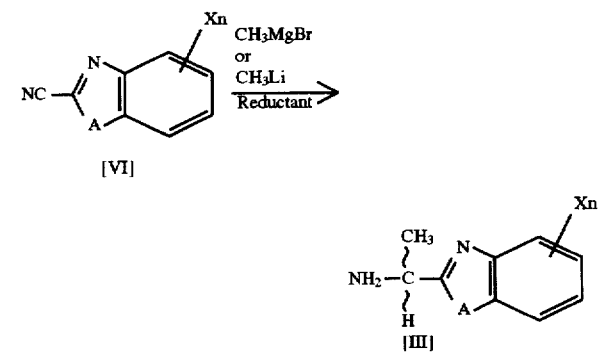

wherein X, A, and n have the same meanings as defined above.

In addition, the compounds represented by Formula [III] can be manufactured according to the following reaction schemes:

Preparation Process B for Starting Material

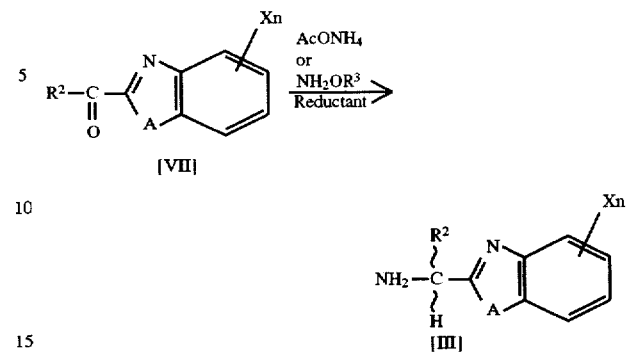

wherein R², X, A, and n have the same meanings as defined above, R³ represents a hydrogen atom or an alkyl group, and Ac represents an acetyl group.

Preparation Process C for Starting Material

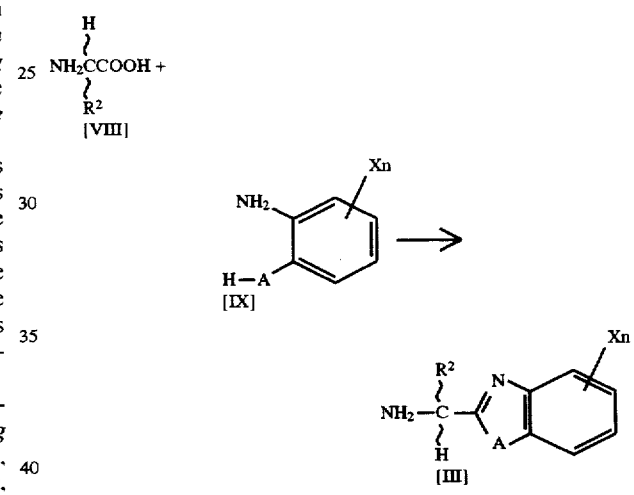

wherein R², X, A, and n have the same meanings as defined above.

Compounds represented by Formula [III] can be also manufactured by means of the reaction of compounds represented by Formula [VIII] having either the protected amino groups of the amino acid moieties or the activated carboxyl groups of the amino acid moieties, with anilines represented by Formula [IX], in the presence of catalysts and/or bases when required, followed by deprotecting the amino protecting groups of the amino acid moieties. The deprotection may be carried out by means of the widely known methods, for example, a catalytic reduction, or an acid treatment method using acids such as liquid hydrogen fluoride, sulfonic acids, hydrogen chloride, hydrogen bromide, formic acid, or the like.

Preparation Process D for Starting Material

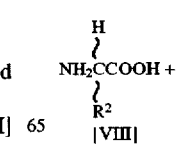

-continued

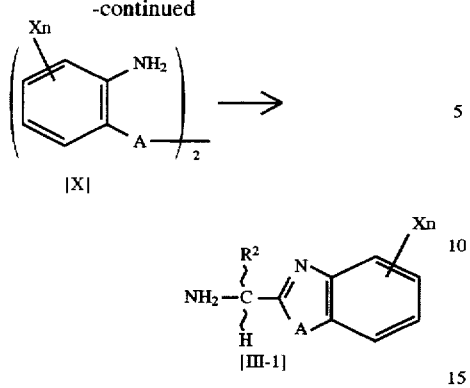

wherein $R^2$, X, and n have the same meanings as defined above, and A represents a sulfur atom.

Compounds represented by Formula [III-1] can be also manufactured by means of the reaction of compounds represented by Formula [VIII] having either the protected amino groups of the amino acid moieties or the activated carboxyl groups of the amino acid moieties, with aminophenyl disulfides represented by Formula [X], in the presence of catalysts and/or bases when required, followed by reduction of the products using reductants and then deprotection of the amino protecting groups of the amino acid moieties. The deprotection may be carried out by means of the widely known methods, for example, a catalytic reduction, or an acid treatment method using acids such as liquid hydrogen fluoride, sulfonic acids, hydrogen chloride, hydrogen bromide, formic acid, or the like.

In these preparation processes for starting materials, as the amino protecting group of the amino acid moiety represented by Formula [VIII], there can be mentioned, for example, a urethane-type protecting group such as a tert-butoxycarbonyl group, a benzyloxycarbonyl group, or the like, an acyl-type protecting group such as a formyl group, a phthaloyl group, or the like, or an alkyl-type protecting group such as a triphenylmethyl group or the like.

As the compound possessing the activated carboxylic group, there can be mentioned an acid halide such as an acid chloride or the like, an acid anhydride derived by dehydration-condensation of the two molecules of the amino acid derivatives represented by Formula [VIII], a mixed acid anhydride derived from the amino acid derivative represented by Formula [VIII] and another acid or an O-alkyl carbonic acid, and an activated ester such as p-nitrophenyl ester, 2-tetrahydropyranyl ester, 2-pyridyl ester and the like.

In addition, it is also possible to perform the reactions represented by Preparation Processes C and D for starting materials using a condensing agent such as N,N'-dicyclohexylcarbodiimide, N,N'-carbonyldiimidazole, 2-chloro-1,3-dimethylimidazolium chloride, or the like.

Preparation Process B

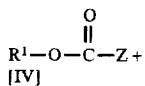
[IV]

-continued
Preparation Process B

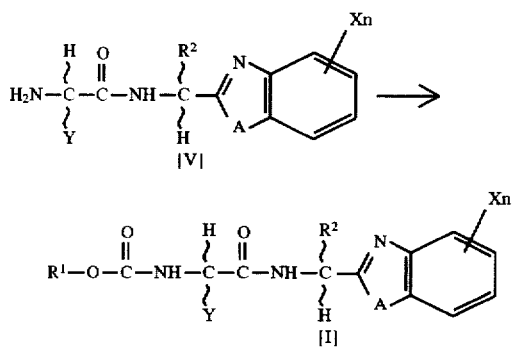

wherein $R^1$, $R^2$, X, Y, A, and n have the same meanings as defined above, and Z represents a halogen atom or a group of the formula: $R^1OC(O)O$—.

The compounds represented by Formula [I] according to the present invention can be prepared by the reaction of compounds represented by Formula [IV] with amines represented by Formula [V], inorganic salts thereof such as hydrochloride or the like or organic acid salts thereof such as tosylate or the like in the presence of bases, if necessary.

The present reaction is usually carried out in a solvent. As a solvent, there can be mentioned, for example, hydrocarbons such as pentane, hexane, heptane, cyclohexane, petroleum ether, ligroin, benzene, toluene, xylene and the like, halogenated hydrocarbons such as methylene chloride, dichloroethane, chloroform, carbon tetrachloride, chlorobenzene, dichlorobenzene and the like, ethers such as diethyl ether, diisopropyl ether, ethylene glycol dimethyl ether, tetrahydrofuran, dioxane and the like, ketones such as acetone, methyl ethyl ketone, methyl isopropyl ketone, methyl isobutyl ketone and the like, acetates such as methyl acetate, ethyl acetate and the like, nitriles such as acetonitrile, propionitrile, benzonitrile and the like, aprotic polar solvents such as dimethylsulfoxide, N,N-dimethylformamide, sulfolane and the like, water, and mixed solvents combining solvents selected from the aforementioned.

The base can be any type of base generally used in this type of reaction. For example, there can be mentioned hydroxides of alkaline metals such as sodium hydroxide, potassium hydroxide and the like, hydroxides of alkaline earth metals such as calcium hydroxide and the like, carbonates of alkaline metals such as sodium carbonate, potassium carbonate and the like, organic bases such as triethylamine, trimethylamine, N,N-dimethylaniline, N-methylmorpholine, pyridine, N-methylpiperidine, 1,5-diazabicyclo [4.3.0] non-5-ene (DBN), 1,8-diazabicyclo [5.4.0] undec-7-ene (DBU), and the like, and preferably tertiary amines such as triethylamine, N-methylmorpholine, pyridine, N-methylpiperidine and the like.

The present reaction is carried out at a temperature range of from −20° C. to 100° C., and preferably from −20° C. to 40° C. The reaction time is preferably 0.5 to 20 hours.

Next, the preparation processes for starting materials for use in the present reaction will be explained.

Condensed hetero-cycle derivatives represented by Formula [V] can be prepared, for example, by treating a carbamate of the compound represented by Formula [I] synthesized using Preparation Process A, according to a conventional method for deprotecting an amino protecting group of an amino acid moiety, such as catalytic reduction or acid-treatment using liquid hydrogen fluoride, a sulfonic acid, hydrogen chloride, hydrogen bromide, formic acid, or the like.

In addition, compounds represented by Formula [IV] can be prepared, for example, using a corresponding alcohol or phenol and a phosgene.

In the following, Preparation Examples of compounds represented by Formula [III] as starting material are provided as reference examples.

REFERENCE EXAMPLE 1

Preparation of (R,S)-1-(5-Fluoro-2-benzimidazolyl) ethylamine 135.8 g of ammonium acetate and 7.8 g of sodium cyanoborohydride were added to a solution containing 31.4 g of 2-acetyl-5-fluorobenzimidazole dissolved in 500 mL of methanol, and the reaction mixture was stirred for 15 hours at room temperature. The resulting mixture was then concentrated under reduced pressure, and acidified with concentrated hydrochloric acid. Diethyl ether was then added thereto. Subsequently, the water layer was made basic with a 5% aqueous solution of sodium hydroxide, the solution was extracted with ethyl acetate, and then washed with water. The organic layer was then dried over anhydrous sodium sulfate, and the solvent was removed under reduced pressure. The obtained residue was purified by column chromatography on silica gel to obtain 6.2 g of the desired product (yield: 20%).

| $^1$H-NMR; (CDCl$_3$, δ) | |
| --- | --- |
| 1.57 | (3H, d) |
| 4.39 | (1H, q) |
| 5.10 | (3H, bs) |
| 7.08–7.52 | (3H, m) |

REFERENCE EXAMPLE 2

Preparation of (R)-1-(4-Chloro-2-benzothiazolyl) ethylamine 18.4 g of N,N'-carbonyldiimidazole was gradually added to a solution containing 20.5 g of N-tert-butoxycarbonyl-D-alanine dissolved in 200 mL of tetrahydrofuran, and the reaction mixture was stirred for 30 minutes at room temperature. 16.5 g of 2-amino-3-chlorothiophenol was added to the reaction mixture, and the whole mixture was refluxed for 3 hours. After completion of the reaction, the resulting mixture was poured into ice-cold water. The organic layer was extracted with ethyl acetate, washed using water, and then dried over anhydrous sodium sulfate. The solvent was removed under reduced pressure. The residue was purified by column chromatography on silica gel, thus yielding 16.8 g of (R)-N-tert-butoxycarbonyl-1-(4-chloro-2-benzothiazolyl)ethylamine (melting point: 95°–96° C.). Furthermore, a hydrogen chloride gas was bubbled into a solution containing 10 g of the crystals obtained above dissolved in 50 mL of methylene chloride, for 3 hours at room temperature. After completion of the reaction, the reaction mixture was extracted with water, and was made basic using a saturated aqueous solution of sodium bicarbonate. The solution was extracted with ethyl acetate, washed with water, and then dried over anhydrous magnesium sulfate, followed by concentration under reduced pressure. The residue was purified by column chromatography on silica gel to afford 5.7 g (yield 84%) of the desired product.

| $^1$H-NMR; (CDCl$_3$, δ) | |
| --- | --- |
| 1.60 | (3H, d) |
| 1.89 | (2H, s) |
| 4.55 | (1H, q) |
| 7.17–7.76 | (3H, m) |

REFERENCE EXAMPLE 3

Preparation of (R)-1-(6-Methyl-2-benzothiazolyl) ethylamine 11.5 g of N,N'-carbonyldiimidazole was gradually added to a solution containing 12.8 g of N-tert-butoxycarbonyl-D-alanine dissolved in 100 mL of tetrahydrofuran, and the reaction mixture was stirred for 30 minutes. 8.9 g of 2-amino-5-methylphenyldisulfide was added to the reaction mixture, and the whole mixture was refluxed for 3 hours. After completion of the reaction, the resulting mixture was poured into ice-cold water. The solution was extracted with ethyl acetate, washed using water, and then dried over anhydrous magnesium sulfate. The solvent was removed under reduced pressure. 1.2 g of lithium aluminum hydride was gradually added to a solution containing the crude 2-[N-(N'-tert-butoxycarbonyl-D-alanyl)] amino-5-methylphenyldisulfide obtained above dissolved in 100 mL of tetrahydrofuran, and the reaction mixture was stirred for 15 hours at room temperature. The reaction mixture was poured into 10% hydrochloric acid. The solution was extracted with ethyl acetate, washed successively with a saturated aqueous solution of sodium bicarbonate and water, and then dried over anhydrous magnesium sulfate. The solvent was removed under reduced pressure. The residue was purified by column chromatography on silica gel to afford 3 g of (R)-N-tert-butoxycarbonyl-1-(6-methyl-2-benzothiazolyl)ethylamine (melting point: 101°–104° C.). Furthermore, hydrogen chloride gas was bubbled into a solution containing the crystals obtained above dissolved in 30 mL of methylene chloride, for 3 hours at room temperature. After completion of the reaction, the solvent was removed under reduced pressure. The residue was made basic by means of adding a saturated aqueous solution of sodium bicarbonate. The solution was extracted with ethyl acetate, washed with water, and dried over anhydrous magnesium sulfate. The solvent was removed under reduced pressure. The residue was purified by column chromatography on silica gel to afford 1.3 g (yield: 11%) of the desired product.

| $^1$H-NMR; (CDCl$_3$, δ) | |
| --- | --- |
| 1.59 | (3H, d) |
| 1.90 | (2H, s) |
| 2.42 | (3H, s) |
| 4.45 | (1H, q) |
| 7.05–7.90 | (3H, m) |

Next, the Preparation Examples for the compounds represented by Formula [V] as starting materials will be explained.

REFERENCE EXAMPLE 4

Preparation of $N^1$-[(R)-1-(2-Benzothiazolyl)ethyl]-L-valinamide

A hydrogen chloride gas was bubbled into a solution containing 0.6 g of $N^2$-tert-butoxycarbonyl-$N^1$-[(R)-1-(2- benzothiazolyl)ethyl]-L-valinamide dissolved in 20 mL of methylene chloride for one hour at room temperature. After completion of the reaction, 50 mL of water was added to the reaction mixture, and the whole mixture was vigorously stirred. The water layer was made basic using a saturated aqueous solution of sodium bicarbonate. The solution was extracted with ethyl acetate, washed with water, and then dried over anhydrous magnesium sulfate. The solvent was removed under reduced pressure to afford 0.44 g (yield: 100%) of the desired product.

| $^1$H-NMR; (CDCl$_3$, δ) | |
| --- | --- |
| 0.93 | (6H, t) |
| 1.59 | (2H, s) |
| 1.69 | (3H, d) |
| 2.33 | (1H, m) |
| 3.28 | (1H, d) |
| 5.49 | (1H, dq) |
| 7.16–8.03 | (4H, m) |
| 8.13 | (1H, bs) |

BEST MODE FOR CARRYING OUT THE INVENTION

The methods for producing the compounds according to the present invention will be described in detail in the following Preparation Examples.

PREPARATION EXAMPLE 1

Preparation of $N^1$-[(R)-1-(6-Fluoro-2-benzothiazolyl)ethyl]-$N^2$-isopropoxycarbonyl-L-valinamide (Compound No. 4)

0.4 g of N-methylpiperidine was added to a solution containing 0.8 g of N-isopropoxycarbonyl-L-valine dissolved in 25 ml of methylene chloride, at −20° C. After the mixture was stirred for 10 minutes at the same temperature, 0.6 g of isobutyl chloroformate was added to the mixture at −20° C., and stirred for 1 hour at −20° C.—10° C. After 0.8 g of (R)-1-(6-fluoro-2-benzothiazolyl)ethylamine was added to this mixture at −60° C., the refrigerant was put off, and then the reaction mixture was warmed naturally to room temperature while being stirred. After completion of the reaction, the resulting mixture was washed successively with water, a 5% aqueous solution of sodium bicarbonate, and water. The organic layer was dried over anhydrous magnesium sulfate, and then the solvent was removed under reduced pressure. The obtained crude crystals were purified by column chromatography on silica gel, thus yielding 0.95 g of the desired product in the form of a white powder (yield: 63%).

PREPARATION EXAMPLE 2

Preparation of $N^1$-[(R)-1-(4-Chloro-2-benzothiazolyl)ethyl]-$N^2$-isopropoxycarbonyl-L-valinamide (Compound No. 7)

0.5 g of N-methylpiperidine was added to a solution containing 0.96 g of N-isopropoxycarbonyl-L-valine dissolved in 50 mL of methylene chloride, at −20° C. and the mixture was stirred for 10 minutes at the same temperature. Subsequently 0.6 g of isobutyl chloroformate was added to the mixture at −20° C., and then stirred for 30 minutes at the same temperature. 1.0 g of (R)-1-(4-chloro-2-benzothiazolyl)ethylamine was added to the reaction mixture at −60° C. The whole mixture was stirred for 15 hours at room temperature. After completion of the reaction, the resulting mixture was washed successively with water, a 5% aqueous solution of sodium bicarbonate, and water. The organic layer was dried over anhydrous magnesium sulfate, and then the solvent was removed under reduced pressure. The obtained crude crystals were purified by column chromatography on silica gel, thus yielding 0.35 g of the desired product in the form of a colorless powder (yield: 19%).

PREPARATION EXAMPLE 3

Preparation of $N^2$-tert-Butoxycarbonyl-$N^1$-[(R)-1-(6-chloro-2-benzothiazolyl)ethyl]-L-valinamide (Compound No. 21)

0.37 g of N-methylpiperidine was added to a solution containing 0.8 g of N-tert-butoxycarbonyl-L-valine dissolved in 50 mL of methylene chloride, at −20° C. After the mixture was stirred for 10 minutes at the same temperature, 0.51 g of isobutyl chloroformate was added to the mixture at −20° C., and stirred for 30 minutes at −20° C. After 0.8 g of (R)-1-(6-chloro-2-benzothiazolyl)ethylamine was added to this mixture at −60° C., the refrigerant was put off, and then the reaction mixture was warmed naturally to room temperature, with stirring, and stirred for 15 hours at room temperature. After completion of the reaction, the resulting mixture was washed successively with water, a 5% aqueous solution of sodium bicarbonate, and water. The organic layer was dried over anhydrous magnesium sulfate and the solvent was removed under reduced pressure. The residue, which was a crude crystal, was purified by column chromatography on silica gel, thus yielding 1.3 g of the desired product in the form of a colorless prism (yield: 87%).

PREPARATION EXAMPLE 4

Preparation of $N^2$-tert-Butoxycarbonyl-$N^1$-[1-(5-fluoro-2-benzimidazolyl)ethyl]-L-valinamide (Compound No. 24)

1.1 g of N-methylpiperidine was added to a solution containing 2.4 g of N-tert-butoxycarbonyl-L-valine dissolved in 100 mL of methylene chloride, at −20° C., and then the mixture was stirred for 10 minutes at the same temperature. Subsequently, 1.5 g of isobutyl chloroformate was added to the mixture at −20° C., and then stirred for 30 minutes at −20° C. After 2.0 g of 1-(5-fluoro-2-benzimidazolyl)ethylamine was added to this mixture at −60° C. and the refrigerant was put off, the reaction mixture was stirred for 15 hours at room temperature. After completion of the reaction, the reaction mixture was washed successively with water, a 5% aqueous solution of sodium bicarbonate, and water. The organic layer was dried over anhydrous magnesium sulfate and the solvent was removed under reduced pressure. The residue, which was a crude crystal, was purified by column chromatography on silica gel, thus yielding 2.5 g of the desired product in the form of colorless needles (yield: 60%).

PREPARATION EXAMPLE 5

Preparation of $N^1$-[1-(2-Benzothiazolyl)ethyl]-$N^2$-isopropoxycarbonyl-L-valinamide (Compound No. 31)

0.3 g of N-methylpiperidine was added to a solution containing 0.6 g of N-isopropoxycarbonyl-L-valine dissolved in 40 mL of methylene chloride, at −20° C., and then the mixture was stirred for 10 minutes at the same temperature. 0.4 g of isobutyl chloroformate was added to the mixture at −40° C., and then stirred for 1 hour at −40° C. to −15° C. After 0.5 g of 1-(2-benzothiazolyl)ethylamine was added to this mixture at −60° C. and the refrigerant was put off, the reaction mixture was warmed naturally to room temperature while being stirred. After completion of the reaction, the reaction mixture was washed successively with water, a 5% aqueous solution of sodium bicarbonate, and water. The organic layer was dried over anhydrous magnesium sulfate and the solvent was removed under reduced pressure. The residue, which was a crude crystal, was purified by column chromatography on silica gel, thus yielding 0.6 g of the desired product in the form of a white powder (yield: 59%).

PREPARATION EXAMPLE 6

Preparation of $N^1$-[1-(2-Benzoxazolyl)ethyl]-$N^2$-isopropoxycarbonyl-L-valinamide (Compound No. 57)

0.3 g of N-methylpiperidine was added to a solution containing 0.6 g of N-isopropoxycarbonyl-L-valine dissolved in 30 mL of methylene chloride, at –20° C., and then the mixture was stirred for 15 minutes at the same temperature. 0.4 g of isobutyl chloroformate was added to the mixture at –30° C., and then stirred for 30 minutes at –30° C. to –20° C. After 0.5 g of 1-(2-benzoxazolyl)ethylamine was added to this mixture at –50° C. and the refrigerant was put off, the reaction mixture was stirred for 15 hours at room temperature. After completion of the reaction, the reaction mixture was washed with water. The organic layer was dried over anhydrous magnesium sulfate and the solvent was removed under reduced pressure. The residue, which was a crude crystal, was purified by column chromatography on silica gel, thus yielding 0.4 g of the desired product in the form of a white powder (yield: 39%).

PREPARATION EXAMPLE 7

Preparation of $N^1$-[(R)-1-(2-Benzothiazolyl)ethyl]-$N^2$-isopropoxycarbonyl-L-valinamide (Compound No. 32)

0.7 g of N-methylpiperidine was added to a solution containing 1.5 g of N-isopropoxycarbonyl-L-valine dissolved in 25 mL of methylene chloride, at –20° C., and then the mixture was stirred for 10 minutes at the same temperature. Subsequently, 1.0 g of isobutyl chloroformate was added to the mixture at –40° C., and then stirred for 1 hour at –40° C. to –15° C. After 1.3 g of (R)-1-(2-benzothiazolyl) ethylamine was added to this mixture at –60° C. and the refrigerant was put off, the reaction mixture was warmed naturally to room temperature while being stirred.

After completion of the reaction, the reaction mixture was washed successively with water, a 5% aqueous solution of sodium bicarbonate, and water. The organic layer was dried over anhydrous magnesium sulfate and the solvent was removed under reduced pressure. The residue, which was a crude crystal, was purified by column chromatography on silica gel, thus yielding 0.5 g of the desired product in the form of a white powder (yield: 19%).

PREPARATION EXAMPLE 8

Preparation of $N^1$-[1-(5-Chloro-2-benzothiazolyl)ethyl]-$N^2$-phenoxycarbonyl-L-valinamide (Compound No. 91)

0.24 g of N-methylpiperidine was added to a solution containing 0.4 g of $N^1$-[1-(5-chloro-2-benzothiazolyl)ethyl]-L-valinamide hydrochloride dissolved in 30 ml of methylene chloride, at –50° C. After the mixture was stirred for 10 minutes at the same temperature, 0.19 g of phenyl chloroformate was added to the mixture at –50° C., and subsequently the refrigerant was put off. Subsequently, the reaction mixture was stirred for 15 hours at room temperature. After completion of the reaction, the resulting mixture was washed with water. The organic layer was dried over anhydrous magnesium sulfate and the solvent was removed under reduced pressure. The residue, which was a crude crystal, was purified by column chromatography on silica gel, thus yielding 0.35 g of the desired product in the form of a white powder (yield: 70%).

PREPARATION EXAMPLE 9

Preparation of $N^2$-tert-Butoxycarbonyl-$N^1$-[1-(1-methyl-2-benzimidazolyl)ethyl]-L-valinamide (Compound No. 65)

0.19 g of N-methylpiperidine was added to a solution containing 0.41 g of N-tert-butoxycarbonyl-L-valine dissolved in 40 mL of methylene chloride, at –20° C., and subsequently the mixture was stirred for 10 minutes at the same temperature. 0.26 g of isobutyl chloroformate was added to the mixture at –40° C., and then the entire mixture was stirred for 1 hour at –40° C.—15° C. After 0.33 g of 1-(1-methyl-2-benzimidazolyl)ethylamine was added to this mixture at –60° C. and the refrigerant was put off, the reaction mixture was warmed naturally to room temperature while being stirred. After completion of the reaction, the reaction mixture was washed successively with water, a 5% aqueous solution of sodium bicarbonate, and water. The organic layer was dried over anhydrous magnesium sulfate and the solvent was removed under reduced pressure. The residue, which was a crude crystal, was purified by column chromatography on silica gel, thus yielding 0.53 g of the desired product in the form of a white powder (yield: 76%).

The agricultural or horticultural fungicides according to the present invention include amino acid amide derivatives represented by Formula [I] as active ingredients. In the case where the compounds according to the present invention are employed as agricultural or horticultural fungicides, the compounds acting as the active ingredients can be formulated appropriately, depending on the purpose, although they may be employed per se. The active ingredient is usually diluted in an inert liquid or a solid carrier, and a surfactant or the like is added thereto, if necessary. The mixture is then formulated in a known manner into, for example, a fine powder, a wettable powder, an emulsifiable concentrate, granules, or the like.

The proportion of the active ingredient is selected as needed. When formulated into a fine powder or granules, 0.1% by weight to 20% by weight of the active ingredient is preferred. For an emulsifiable concentrate or wettable powder, 5% by weight to 80% by weight of the active ingredient is preferred.

As the suitable carriers employed in the formulation, there can be mentioned solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like.

As the surfactants and dispersants, there can be mentioned dinaphthylmethane disulfonate, alcohol sulfates, alkyl aryl sulfonates, ligninesulfonates, polyoxyethylene glycol ethers, polyoxyethylene alkyl aryl ethers, polyoxyethylene sorbitan monoalkylates, and the like.

As the auxiliary agents, there can be mentioned carboxymethylcellulose, and the like.

The formulated agricultural or horticultural fungicides according to the present invention can be spread in an appropriate diluted concentration or can be applied directly.

The rate of application of the agricultural or horticultural fungicides according to the present invention may vary depending on the type of active compound employed, the kind of the pest or disease to be controlled, the tendency of occurrence of the pest or disease, the degree of damage, environmental conditions, the form of preparation to be used, and the like. When the agricultural or horticultural fungicides of the present invention are applied directly in the form of fine powder or granules, it is recommended that the rate of application of the active ingredients be suitably chosen within the range of from 0.1 g to 5 kg per 10 ares, preferably, in the range of from 1 g to 1 kg per 10 ares. In addition, when the fungicides of the present invention are applied in the form of a liquid such as an emulsifiable concentrate or a wettable powder, it is recommended that the ratio for application of the active ingredients be suitably chosen within the range of from 0.1 ppm to 5,000 ppm, and preferably within the range of from 1 ppm to 1,000 ppm.

The agricultural or horticultural fungicides according to the present invention can be employed for a number of purposes: for example, treating seeds, spraying of stem and leaf portions, applying to the soil, and submerged application. The agricultural or horticultural fungicides of the present invention can control plant diseases caused by fungi in the Oomycetes, Ascomycetes, Deuteromycetes, and Basidiomycetes or other pathogenic fungi.

The fungi include, but are not limited to, Phytophthora such as tomato late blight (Phytophthora infestans), Plasmopara such as grape downy mildew (Plasmopara viticola), and Pseudoperonospora such as cucumber downy mildew (Pseudoperonospora cubensis).

The compounds according to the present invention may be employed alone or in combination with other fungicides, insecticides, herbicides, plant growth modifiers, fertilizers or the like.

Next, the representative formulations are illustrated with reference to the following Formulation Examples, wherein all "%" represent "percent by weight".

FORMULATION EXAMPLE 1

Fine Powder

2% of Compound No. 1, 5% of diatomaceous earth, and 93% of clay were uniformly mixed and ground into a fine powder.

FORMULATION EXAMPLE 2

Wettable Powder

50% of Compound No. 9, 45% of diatomaceous earth, 2% of sodium dinaphthylmethanedisulfonate, and 3% of sodium ligninsulfonate were uniformly mixed and ground into a wettable powder.

FORMULATION EXAMPLE 3

Emulsifiable Concentrate

30% of Compound No. 18, 20% of cyclohexanone, 11% of polyoxyethylene alkyl aryl ether, 4% of calcium alkylbenzenesulfonate, and 35% of methylnaphthalene were uniformly dissolved, thus yielding an emulsifiable concentrate.

FORMULATION EXAMPLE 4

Granules

5% of Compound No. 26, 2% of sodium lauryl alcohol sulfate, 5% of sodium ligninsulfonate, 2% of carboxymethylcellulose, and 86% of clay were mixed and ground. 20% of water was added to the ground mixture. The resulting mixture was kneaded and formed into granules of 14 mesh to 32 mesh by means of an extrusion granulator, and then dried into the desired granules.

EFFECTS OF THE INVENTION

The agricultural or horticultural fungicides according to the present invention exhibit high ability to prevent fungal infection caused by tomato late blight (Phytophthora infestans), potato late blight (Phytophthora infestans), grape downy mildew (Plasmopara viticola), and cucumber downy mildew (Pseudoperonospora cubensis). In addition, the agricultural or horticultural fungicides according to the present invention not only exhibit the ability to prevent fungal infection, but also exhibit the ability to eliminate pathogenic fungi after it has invaded a host plant.

Furthermore, the agricultural or horticultural fungicides of the present invention are also characterized in that they are not harmful chemicals and exhibit excellent characteristics such as systemic action, residual activity, and persistence after rainfall.

The effects of the compounds according to the present invention are now illustrated with reference to the following Test Examples. In the Test Examples, the compounds disclosed in European Patent No. 587110 are employed as Comparative Compounds.

Comparative Compound A: $N^2$-tert-butoxycarbonyl-$N^1$-[1-(1,3-dimethyl-2-indolyl)ethyl] -L-valinamide Comparative Compound B: $N^2$-tert-butoxycarbonyl-$N^1$-[1-(3-methyl-2-indolyl)ethyl]-L-valinamide Comparative Compound C: $N^2$-benzyloxycarbonyl-$N^1$-[-(5-chloro-1-methyl-2-indolyl)ethyl]-L-valinamide Comparative Compound D: $N^2$-tert-butoxycarbonyl-$N^1$-[1-(5-chloro-3-methyl-2-benzo[b]thienyl)ethyl] -L-valinamide Comparative Compound E: $N^1$-[1-(2-benzo[b]thienyl)ethyl]-$N^2$-benzyloxycarbonyl-L-valinamide Comparative Compound F: $N^2$-tert-butoxycarbonyl-$N^1$-[1-(3-chloro-2-benzofuranyl)ethyl]-L-valinamide Comparative Compound G: $N^1$-[1-(5-chloro-2-benzofuranyl)ethyl]-$N^2$-methoxycarbonyl-L-valinamide

TEST EXAMPLE 1

Test on the Effect of Preventing Infection by Tomato Late Blight (Phytophthora infestans)

One tomato seedling (variety: "Ponterosa") was transplanted into each ceramic pot (diameter: 12 cm) and grown in a greenhouse. A wettable powder prepared as in Formulation Example 2 was diluted with water to a concentration of 500 ppm of the active ingredient, and the aqueous preparation obtained was then applied at a rate of 20 ml per pot to the tomato seedlings at their 6- or 7-leaf stage. After drying in the air, the plant was inoculated with a zoosporangium suspension of tomato late blight (Phytophthora infestans) fungi by spraying and then placed in a moist chamber at 22° C. On the fourth day after the inoculation, the affected area was measured.

The incidence index of a disease was determined based on the size of the affected area as shown in Table 2. The degree of damage was calculated according to Equation (1) and the ability to prevent the disease (controlling activity) was calculated according to Equation (2). The results are shown in Table 3.

TABLE 2

| Incidence Index | Affected Area |
|---|---|
| 0 | No lesions |
| 1 | Less than 5% |
| 2 | 5% or more and less than 33.3% |
| 3 | 33.3% or more and less than 66.6% |
| 4 | 66.6% or more |

$$\text{Degree of Damage (\%)} = \frac{\Sigma \text{ (Incidence Index} \times \text{Number of Corresponded Leaves)}}{\text{Number of Leaves Examined} \times 4} \times 100$$

$$\text{Controlling Activity (\%)} = \left(1 - \frac{\text{Degree of Damage in Treated Plot}}{\text{Degree of Damage in Untreated Plot}}\right) \times 100$$

TABLE 3

| Compound No. | Controlling Activity (%) |
|---|---|
| 1 | 100 |
| 4 | 100 |
| 6 | 100 |
| 7 | 100 |
| 9 | 100 |
| 10 | 100 |
| 13 | 100 |
| 15 | 100 |
| 17 | 100 |
| 18 | 100 |
| 19 | 100 |
| 21 | 100 |
| 22 | 100 |
| 24 | 100 |
| 31 | 100 |
| 32 | 100 |
| 34 | 100 |
| 61 | 100 |
| 62 | 100 |
| 89 | 100 |
| 90 | 100 |
| 111 | 100 |
| 112 | 100 |
| 113 | 100 |
| 114 | 100 |
| 115 | 100 |
| Comparative Compound A | 0 |
| Comparative Compound B | 0 |
| Comparative Compound C | 0 |
| Comparative Compound D | 15 |
| Comparative Compound E | 0 |
| Comparative Compound F | 0 |
| Comparative Compound G | 25 |

TEST EXAMPLE 2

Test on the Effect of Preventing Infection by Grape Downy Mildew (*Plasmopara viticola*)

Rooted grape cuttings (variety: "Kyoho") were each grown from a cutting, pruned, grown in a ceramic pot (diameter: 12 cm), and maintained in a greenhouse. A wettable powder prepared as in Formulation Example 2 was diluted with water to a concentration of 500 ppm of the active ingredient, and the aqueous preparation obtained was then applied at a rate of 20 ml per pot to the grape seedlings at their 4- or 5-leaf stage. After drying in the air, the plant was inoculated with a zoosporangium suspension of grape downy mildew (*Plasmopara viticola*) fungi by spraying and then placed in a moist chamber at 22° C. for 24 hours, then the pot was placed in a greenhouse to be affected. On the seventh day in the greenhouse after the inoculation, the plant was again placed in a moist chamber at 22° C. for 24 hours to cultivate conidiospores. The incidence area where conidiospores grew on each leaf was examined.

The incidence index determined according to the standards shown in Table 2. The degree of damage was calculated according to the Equation mentioned above using the incidence index and the number of the infected leaves. In addition, the ability to prevent the disease (controlling activity) was calculated according to the Equation mentioned above. The results of the test are shown in Table 4.

TABLE 4

| Compound No. | Controlling Activity (%) |
|---|---|
| 1 | 100 |
| 4 | 100 |
| 6 | 100 |
| 7 | 100 |
| 9 | 100 |
| 10 | 100 |
| 13 | 100 |
| 15 | 100 |
| 17 | 100 |
| 18 | 100 |
| 19 | 100 |
| 21 | 100 |
| 22 | 100 |
| 24 | 100 |
| 31 | 100 |
| 32 | 100 |
| 34 | 100 |
| 61 | 100 |
| 62 | 100 |
| 89 | 100 |
| 90 | 100 |
| 111 | 100 |
| 112 | 100 |
| 113 | 100 |
| 114 | 100 |
| 115 | 100 |
| Comparative Compound A | 0 |
| Comparative Compound B | 0 |
| Comparative Compound C | 0 |
| Comparative Compound D | 12 |
| Comparative Compound E | 0 |
| Comparative Compound F | 0 |
| Comparative Compound G | 18 |

TEST EXAMPLE 3

Test on the Effect of Preventing Infection by Cucumber Downy Mildew (*Pseudoperonospora cubensis*)

Cucumber seeds (variety: "Sagami hanjiro") were sown at a rate of 10 seeds each in a square PVC (polyvinyl chloride) pot, wherein each side is 9 cm wide. The seeds were allowed to grow in a greenhouse, for 7 days, to the cotyledonous stage. A wettable powder prepared as in Formulation Example 2 was diluted with water to a concentration of 500 ppm of the active ingredient, and the aqueous preparation obtained was then applied at a rate of 10 ml per pot to the cucumber seedlings at their cotyledonous stage. After drying in the air, the plant was inoculated with a spore suspension of cucumber downy mildew (*Pseudoperonospora cubensis*) fungi using a spray and then placed in a moist chamber at 22° C. for 24 hours, and then placed in a greenhouse. On the seventh day after the inoculation, the extent of lesions was evaluated.

The results of the test evaluated in accordance with the standards of evaluation as shown in Table 5 are given in Table 6.

TABLE 5

| Standard of evaluation: | Affected area |
| --- | --- |
| Class A: | No lesions were observed |
| Class B: | Affected area is less than 25% |
| Class C: | Affected area is 25% or more and less than 50% |
| Class D: | Affected area is 50% or more |

TABLE 6

| Compound No. | Evaluation |
| --- | --- |
| 1 | A |
| 4 | A |
| 6 | A |
| 7 | A |
| 9 | A |
| 10 | A |
| 13 | A |
| 14 | A |
| 15 | A |
| 17 | A |
| 18 | A |
| 19 | A |
| 21 | A |
| 22 | A |
| 24 | A |
| 25 | A |
| 31 | A |
| 32 | A |
| 34 | A |
| 61 | A |
| 62 | A |
| 64 | A |
| 89 | A |
| 90 | A |
| 111 | A |
| 112 | A |
| 113 | A |
| 114 | A |
| 115 | A |
| Comparative Compound A | D |
| Comparative Compound B | D |
| Comparative Compound C | D |
| Comparative Compound D | D |
| Comparative Compound E | D |
| Comparative Compound F | D |
| Comparative Compound G | D |

TEST EXAMPLE 4

Test on the Effect of Treating Infection by Cucumber Downy Mildew (*Pseudoperonospora cubensis*)

Cucumber seeds (variety: "Sagami hanjiro") were sown at a rate of 10 seeds each in a square PVC (polyvinyl chloride) pot, wherein each side is 9 cm wide. The seeds were allowed to grow in a greenhouse, for 7 days, to the cotyledonous stage. The seedlings were inoculated with a spore suspension of cucumber downy mildew (*Pseudoperonospora cubensis*) fungi by spraying and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a greenhouse. On the seventh day after the inoculation, the extent of lesions was evaluated.

The results of the test evaluated in accordance with the standards of evaluation shown in Table 5 are given in Table 7.

TABLE 7

| Compound No. | Evaluation |
| --- | --- |
| 1 | A |
| 4 | A |
| 6 | A |
| 7 | A |
| 9 | A |
| 10 | A |
| 13 | A |
| 14 | A |
| 15 | A |
| 17 | A |
| 18 | A |
| 19 | A |
| 21 | A |
| 22 | A |
| 24 | A |
| 25 | A |
| 31 | A |
| 32 | A |
| 34 | A |
| 61 | A |
| 62 | A |
| 89 | A |
| 112 | A |
| 113 | A |
| 114 | A |
| 115 | A |
| Comparative Compound A | D |
| Comparative Compound B | D |
| Comparative Compound C | D |
| Comparative Compound D | D |
| Comparative Compound E | D |
| Comparative Compound F | D |
| Comparative Compound G | D |

What is claimed is:

1. An amino-acid amide derivative represented by the formula:

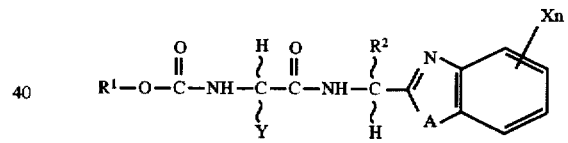

wherein $R^1$ represents C1~C6 alkyl group, a C3~C8 cycloalkyl group, or a phenyl group (optionally having at least one same or different halogen atom substituent), or a benzyl group, $R^2$ represents a hydrogen atom or a methyl group, X represents a halogen atom, a methyl group, a methoxy group, a methylthio group, a cyano group, or a trifluoromethyl group, Y represents a C1~C6 alkyl group, A represents an oxygen atom, a sulfur atom, or a group of the formula:

(wherein $R^3$ represents a C1~C6 alkyl group, a C1~C6 alkoxymethyl group, or an acyl group), and n represents 0 or an integer from 1 to 3, and excluding the derivative wherein A is NH, $R^1$ is $C_1$-alkyl, $R^2$ is hydrogen or methyl, and Y is $C_1$-alkyl.

2. An amino-acid amide derivative as recited in claim 1, wherein $R^1$ represents a C1~C6 alkyl group, $R^2$ represents a hydrogen atom or a methyl group, X represents a halogen atom, a methyl group, or a methoxy group, Y represents a C1-C6 alkyl group, A represents an oxygen atom, a sulfur atom, or a group of the formula:

(wherein $R^3$ represents an acyl group), and n represents 0 or an integer from 1 to 3.

3. An amino-acid amide derivative as recited in claim 1, $R^1$ represents an isopropyl group, $R^2$ represents a methyl group, X represents a fluorine atom, Y represents an isopropyl group, A represents a sulfur atom, and n represents 1.

4. A process for preparing an amino-acid amide derivative represented by the formula:

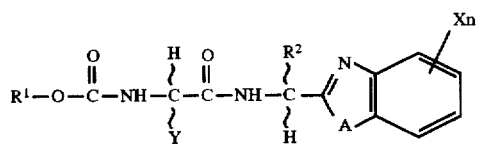

(wherein $R^1$, $R^2$, X, Y, A, and n have the same meanings as defined in claim 1),
comprising a step of reacting an amino-acid amide derivative represented by the formula:

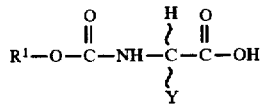

(wherein $R^1$ and Y have the same meanings as defined in claim 1),
or the amino-acid amide derivative possessing an activated carboxyl group, with an amine represented by the formula:

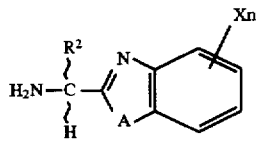

(wherein $R^2$, X, A, and n have the same meanings as defined in claim 1), optionally in the presence of a catalyst and/or a base.

5. A process for preparing an amino-acid amide derivative represented by the formula:

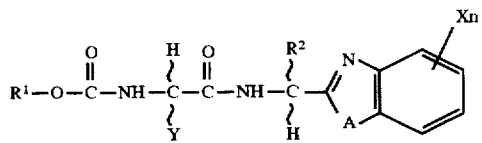

(wherein $R^1$, $R^2$, X, Y, A, and n have the same meanings as defined in claim 1),
comprising a step of reacting a compound represented by the formula:

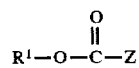

(wherein Z represents a halogen atom or a group of the formula: $R^1OC(O)O-$, $R^1$ has the same meaning as defined in claim 1), with an amine represented by a formula:

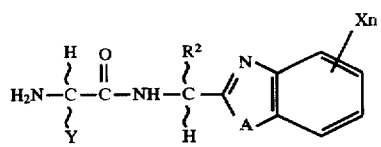

(wherein $R^2$, X, Y, A, and n have the same meanings as defined in claim 1),
or an inorganic acid salt thereof including a hydrochloride or an organic acid salt thereof including a tosylate optionally in the presence of a base.

6. An agricultural or horticultural fungicide including an amino-acid amide derivative as recited in claim 1 as an active ingredient.

7. A method for killing agriculturally or horticulturally harmful fungi which comprises a step of applying to said fungi a fungicidally effective amount of an amino-acid amide derivative as recited in claim 1.

* * * * *